United States Patent
Said et al.

(10) Patent No.: US 7,189,265 B2
(45) Date of Patent: Mar. 13, 2007

(54) COMPOSITION FOR SIMULTANEOUSLY LIGHTENING AND COLORING HAIR UTILIZING BLEACH-STABLE ACID AND BASIC DYES

(75) Inventors: Hayel M. Said, Simi Valley, CA (US); Hian Said, Simi Valley, CA (US)

(73) Assignee: L'Avant Garde, Inc., Simi Valley, CA (US)

( * ) Notice: Subject to any disclaimer, the term of this patent is extended or adjusted under 35 U.S.C. 154(b) by 255 days.

(21) Appl. No.: 10/472,305

(22) PCT Filed: Mar. 18, 2002

(86) PCT No.: PCT/US02/08318

§ 371 (c)(1),
(2), (4) Date: Mar. 9, 2004

(87) PCT Pub. No.: WO02/074270

PCT Pub. Date: Sep. 26, 2002

(65) Prior Publication Data

US 2004/0143910 A1    Jul. 29, 2004

Related U.S. Application Data

(60) Provisional application No. 60/277,080, filed on Mar. 19, 2001.

(51) Int. Cl.
*A61K 7/13* (2006.01)
(52) U.S. Cl. ......... 8/405; 8/406; 8/431; 8/657; 8/658; 8/662; 8/673; 8/676
(58) Field of Classification Search ......... 8/405, 8/406, 431, 657, 658, 662, 673, 676
See application file for complete search history.

(56) References Cited

U.S. PATENT DOCUMENTS 5,474,578 A * 12/1995 Chan et al. ......... 8/431

(Continued)

FOREIGN PATENT DOCUMENTS

DE    2624690    12/1977

(Continued)

OTHER PUBLICATIONS

Dr. G. Schroder BASF Corporation, "Haar und-Pelzfrbung mit oligomeren tiarylmethanfarbstoffen," Research Disclosure, Kenneth Mason Publications (Great Britain), vol. 432 (No. 37), (Apr. 21, 2000).

*Primary Examiner*—Eisa Elhilo
(74) *Attorney, Agent, or Firm*—Hahn Loeser & Parks LLP; John J. Cunniff

(57) ABSTRACT

A composition of certain dyes with a category-2 hair bleach can simultaneously lighten hair up to seven levels and deposit various shades of color in a single step. The dyes are bleach-stable derivatives of azo, triarylmethane, thiazine, or nitro dyes. When linked at the ortho- and/or para-positions relative to the chromophoric centers and auxochrome groups located on or attached to the aromatic rings of these dyes, deactivating or weakly activating chemical groups enhance the dye stability in the alkaline bleach. The absence of ortho and/or para positioned deactivating or weakly-activating substituents, or the presence of strongly activating groups in these positions render the dye molecule susceptible to attack by the bleach and the eventual destruction of these dyes. These deactivating and protective chemical groups may be nitro, halogen, cyano, carboxyl, sulfonic, alkyl or aromatic groups, but not amino, hydroxy, alkoxy or alkylamide groups.

38 Claims, 13 Drawing Sheets

(1)

(2)

(3)

(4)

(5)

(6)

U.S. PATENT DOCUMENTS

| | | | |
|---|---|---|---|
| 5,688,291 A | * | 11/1997 | Said et al. ............... 8/431 |
| 6,440,177 B1 | * | 8/2002 | Orr ........................... 8/426 |
| 2002/0004957 A1 | | 1/2002 | Imperial ................... 8/405 |

FOREIGN PATENT DOCUMENTS

| | | |
|---|---|---|
| DE | 19721785 | 9/1998 |
| DE | 19721785 C1 | 9/1998 |
| FR | 1535799 | 8/1968 |
| GB | 1059986 | 2/1967 |
| GB | 1554331 | 10/1979 |
| GB | 2217735 | 11/1989 |
| JP | 175940/1996 | 7/1996 |
| JP | 09-278634 | 10/1997 |
| WO | WO 0076469 | 12/2000 |
| WO | WO 0152802 | 7/2001 |

\* cited by examiner (1)

(2)

(3)

(4)

(5)

(6)

(7)

(8)

(9)

(10)

(11)

(12)

(13)

(14)

(15)

(16)

(17)

(18)

(19)

(20)

(21)

(22)

(23)

(24)

(25)

(26)

(27)

(28)

(29)

(30)

(31)　　　(31a)　　　(31b)

(32)　　　(33)

(34)

(35)

(36)

(38)

(39)

(40)

(41)

(42)

(43)

(44)

(45)

(46)

(47)

(48)

(49)

(50)

(51)

(52)

(53)

(54)

(55)

(56)

(57)

(58)

(59)

(60)

(61)

(62)

(63)

(64)

(65)

(66)

(67)

(68)

(69)

(70)

(71)

(72)

(73)

(74)

(75)

(76)

(77)

(78)

COMPOSITION FOR SIMULTANEOUSLY LIGHTENING AND COLORING HAIR UTILIZING BLEACH-STABLE ACID AND BASIC DYES

This application claims priority on a provisional application, Ser. No. 60/277,080, filed 19 Mar. 2001.

The present invention pertains generally to hair bleach compositions capable, in a single step, of lightening hair color by as many as seven levels while simultaneously depositing various tones that may either neutralize the warmth generated by the bleaching treatment or add other desirable bright colors to the lightened hair.

BACKGROUND OF THE INVENTION

Natural hair color is derived from melanin granules embedded throughout the cortex of hair fibers. Two general classes of such pigments have been identified: eumelanins (brownish black) and pheomelanins (reddish orange). The combination ratio and concentration of these two types of pigments impart to the hair its characteristic natural gradations of color. Dark hair has a higher concentration of the eumelanins, while red hair has a predominance of the pheomelanins. Light blond hair has reduced amounts of both.

Human hair is arbitrarily assigned a scale of ten levels to describe its darkness (or lightness). Black hair is designated as level one, medium brown hair as level five, and pale light blond as level ten, with several nuances in between.

Hair bleaching is a chemical process by which the melanin pigment granules are gradually destroyed by the bleaching agent, resulting in lighter hair color. The melanin pigments are not all lightened at the same rate. The eumelanins are easier to break down than the pheomelanins. Because of this property, dark hair, when bleached, experiences preferential destruction of the melanin pigments, which leads to the visual enhancement of the red pigments, and the casting of an undesirable warm reddish orange or "brassy" tone to the bleached hair. In order to neutralize this warmth, hair colorants of a drabbing nature are almost always applied during or after a bleaching treatment.

Based on their chemical composition and their strength, hair bleaches may be classified into two groups, designated as Category-1 and Category-2.

Category-1 bleaches are liquid- or cream-based compositions utilizing alkaline hydrogen peroxide solutions as the main oxygen-generating agent to oxidize and bleach hair melanin, usually in conjunction with a hair coloring process. Just before use, the peroxide is mixed with an alkalizing agent such as ammonia, and the resulting liquid or cream is applied to hair for 30 to 60 minutes. Such compositions may lighten the hair by as much as four levels at the most, depending on the concentration of hydrogen peroxide used. For example, a level-6 hair may be lightened, under favorable conditions to a level 10.

Category-2 bleaches are generally powder compositions, some in cream form, which are based on persulfate salts (ammonium, potassium, sodium) as auxiliary or booster supplies of active oxygen, and silicate and/or carbonate salts as sources of alkalinity. Again, just before use, they are mixed with hydrogen peroxide solutions to form a workable cream that can be applied to the hair. It is even possible to have hydrogen peroxide itself incorporated into the powder bleach in a solid form, and all that is needed to achieve a workable cream is to add water to the powder. Quite often, a third separately-packaged component, referred to as a bleach oil, which may contain humectants and other conditioning agents, is added to the bleach powder and peroxide at time of use.

Category-2 bleaches can deliver over seven levels of lift, something which cannot be attained with category-1 bleaches. They are usually utilized whenever more than four levels of lift are desired, such as when lifting a level-5 hair, or darker, to a pale blond. Because of the underlying warm tones that are exposed at various levels of bleaching, a toning process to neutralize the warmth and give the hair a pleasant natural look generally accompanies hair lightening. The toning process itself is a rather delicate one. Toners fall into three hues: blue-green, blue and violet, generally known as drabbing or ashing hues. These hues, or combinations of, are required to neutralize the spectrum of undertones that are exposed during the lightening process. Light brown hair, for example, would expose yellow undertones upon bleaching. Therefore, according to the law of color, a violet-based toner would neutralize the yellowish hue to result in a platinum or silver blond shade. The concentration of the toner should be adjusted so that the lift is not masked by the deposition of color. Similarly, medium brown hair would reveal a significant amount of orange undertones, requiring a significant amount of a blue-based toner. Dark hair, when bleached, exhibits reddish-orange undertones requiring a bluish-green toner.

At other times it is desirable to deposit a bright color on the hair. However, because of the dark pigment in the hair, it is not possible to do that without first bleaching the hair to a lighter color. It is customary therefore to perform a two-step process where the hair is lightened in a first step with category-2 powder bleach, then tinted with a bright color in a second step.

Category-1 bleaches constitute most of what is known as oxidative permanent hair colorants. They contain oxidative dyes. Some may contain Direct, Disperse, Acid, or Basic dyes, or combinations thereof. The prevailing alkaline peroxide environment of this category of bleaches is mild enough to allow for the survival of several types of dyes. Therefore, the limited lightening of hair pigments and the deposition of color is a simultaneous process, which is completed in about an hour.

In category-2 bleaches, the medium is quite intolerant to most dyes. The combination of higher alkalinity and stronger oxidizing conditions, act synergistically to destroy these dyes within a short period of time. Unlike the abundance of colorants surviving category-1 bleaches, only very few dyes have been identified to date which are both, stable in powder bleaches, and capable at the same time of dyeing hair efficiently.

Dyes in general consist of aryl rings or conjugated structures that contain unsaturated chemical groups such as (>C=C<), (>C=N—), (>C=O), (—N=O), or (—N=N—) referred to as chromophores. Weakly basic groups such as (—OH) or (—$NH_2$), called auxochromes, are often attached to the aryl rings and assist in intensifying the color generated by the chromophores. Most chemical groups added to an aryl ring can affect the way the ring may undergo electrophilic substitution. Groups that withdraw electrons are called deactivating groups because once attached to benzene they render the ring less reactive than, the unsubstituted benzene, while others that donate electrons are called activating because the ring they are attached to becomes more active than benzene. Activating groups include hydroxy (—OH), amino (—$NH_2$, —NHR, —$NR_2$), alkoxy groups (—$OCH_3$, —$OC_2H_5$, etc.) and alkylaznide (—NHCOR). Deactivating groups include nitro (—$NO_2$), cyano (—CN), carboxy (—COOH, —COOR), sulfonic (—SO$_3$H), or halide (—F, —Cl, —Br, —I). Activating groups are ortho, para directors because they cause attack on the aryl ring to occur at positions ortho and para to them, while deactivating groups (with the exception of the halogens) are meta directors because chemical attack occurs at the meta position with respect to these groups.

Based on structure, dyes are classified into the following chemical classes: acridine, anthraquinone, azine, azo, cyanine, formazan, indamine, indigoid, nitro, oxazine, phthalocyanine, quinophthalone, stilbene, thiazine, thiazole, triarylmethane, and xanthene.

A triarylmethane dye is built around a basic skeleton where a central methane carbon atom, shown in the drawings as Structure 1, is linked to three aryl nuclei that may be substituted at the para position relative to the central methane carbon, with primary, secondary, or tertiary amino groups, or hydroxy groups, or combination of both. In Structure 1 of the accompanying single figure, X, Y and Z may all be terminal aryl systems, naphthyl systems or combination thereof. Based on this basic plan, triarylmethane dyes may be divided as follows: A) Triphenylmethane dyes, where X, Y and Z in Structure 1 are all aryl derivatives; B) Diphenylnaphthylmethane dyes, where one of X, Y or Z in Structure 1 is a naphthyl group and the remaining group are phenyl groups; and C) Dinaphthylphenylmethane dyes, where two of the rings in Structure 1 are naphthyl groups and the remaining group is a phenyl group.

In absence of any acidic groups on the aromatic rings, triarylmethane dyes are termed cationic or basic dyes. The presence of sulfonic acid groups confers acidic or anionic properties as well as water solubility. In all divisions of the triarylmethanes, some or all of the aryl nuclei are substituted in the para position to the central methane carbon with auxochromes $x^1$, $y^1$, or $z^1$ such that $x^1$, $y^1$, or $z^1$ are hydroxy, amino or both, as in Structure 2. If the auxochrome is an amino group, it may be a primary amino (—NH$_2$), a secondary amino (—NHR$_1$) or a tertiary amino (—NR$_2$), where R$_1$ and R$_2$ may be identical or different, and either may be alkyl, alkoxy, carboxy, cyano, alkyl-cyano, halogen, phenyl, or naphthyl substituent.

Triphenylnethane dyes constitute the majority of the triarylmethane class of dyes. The chromophoric system of these dyes consists of resonance hybrids involving the central carbon atom, which is sp$^2$ hybridized, and the para-amino- or para-hydroxy groups located on the aromatic rings attached to that carbon.

Triarylmethanes may be synthesized via several routes such as the aldehyde synthesis, the hydrol synthesis and the ketone synthesis. In the aldehyde method, different aldehydes may be reacted with suitable aromatic amines, phenols or naphthols to form various amino or hydroxy derivatives. In the hydrol and ketone methods, diaryl hydrols or diaryl ketones may be reacted with suitable aromatic amines or phenols to form a variety of these dyes. In the case of the phenolphthalein and sulfonephthalein dye derivatives, synthesis is achieved by condensing aromatic anhydrides including phthalic anhydride and sulfobenzoic acid cyclic anhydride derivatives with phenols or benzoic acid derivatives.

Based on their chemical constituents therefore, triarylmethane dyes may be classified into at least five subclasses.

The first such subclass comprises monoamino derivatives in which only one aromatic ring contains a para amino auxochrome. An example is Fuchsonimine hydrochloride, CAS# 84215-84-9, shown as Structure 3.

The second subclass comprises the diamino derivatives in which two aromatic rings contain a para amino group. An example is CI Basic Green 4, CI 42000, CAS# 569-64-2, shown as Structure 4.

The third subclass comprises the triamino derivatives of triphenylmethane in which all three aromatic rings contain a para amino auxochrome, an example of which is CI Basic Red 9, CI 42500, CAS# 569-61-9, shown as Structure 5.

The fourth subclass comprises aminohydroxy derivatives where para amino and para hydroxy groups are present on separate aromatic rings, an example of which is CI Mordant Violet 11, CI 43550, shown as Structure 6.

The fifth subclass comprises the hydroxy derivatives, where one or more para hydroxy groups are present on one or more aromatic rings. These include typical ionic members such as CI Mordant Blue 3, CI 43820, CAS# 3564-18-9, shown as Structure 7, as well as nonionic members. The nonionic members are pH-dependent lactone and sultone triphenylmethane derivatives. At lower pH, the dye is in the nonionic lactone or sultone form, which is colorless because the central carbon atom is unable to participate in any resonance structure. At alkaline pH the dye ionizes and undergoes lactone or sultone ring opening to produce a colored stabilized triphenylmethane ion. Members of this division include the phthaleins and sulfonphthaleins families. Phthaleins include phenolphthalein, CAS# 81-90-3, shown as Structure 8, and the sulfonphthaleins include phenol red, CAS# 143-74-8, shown as Structure 9.

Azo dyes are characterized by the presence of one or more azo (—N=N—) groups, which are generally associated with auxocluromes such as amino (—NH—) and hydroxy (—OH) groups as is the case with triarylmethane dyes. The first step in their synthesis is the formation of a diazonium ion or a diazo component, shown as Structure 10, by a diazotation coupling reaction in which a nitrosating agent attacks a benzenoid component such as an arylaminie or a heterocyclic amine in which the amino group is attached to a nitrogen- or sulfur-containing ring. Examples of heterocyclic diazo components include those derived from 2-aminobenzothiazoles and their substituents, shown as Structure 11, 2-amino-5-nitrothiazoles and their substituents (shown as structure 12), 3-aminobenzisothiazoles and their substituents (shown as Structure 13) and thiophenes and their substituents (shown as Structure 14). Because the diazo components are such powerful electrophiles they can readily attack compounds having nucleophilic centers, which are called coupling components, to form azo dyes. Such coupling components include other arylamines as well as phenols, naphthols and keto-enol compounds (acetoacetarylamides, pyridones, pyrazolones, aminopyrazoles). Some examples follow of various azo dyes formed by using different diazo and coupling components:

Structure 15 is an example of an azo dye (C.I. Basic Orange 2) formed by the union of an arylamine-diazo component and an arylamine-coupling agent.

Structure 16 is an example of an azo dye (FD&C Red #40) formed by the union of an arylamine-diazo component and a naphthol-coupling agent.

Structure 17 is an example of an azo dye (C.I. Disperse Blue 156) formed by the union of a benzothiazole diazo component (6-nitro-2-aminobenzothiazole) and an arylamine-coupling agent.

Structure 18 is an example of an azo dye formed by the union of a nitrothiazole diazo component (2-amino-5-nitrothiazole) and an arylamine-coupling agent.

Structure 19 is an example of an azo dye (C.I. Disperse Blue 148) formed by the union of a benzisothiazole diazo component (5-nitro-3-aminobenzisothiazole) and an arylamine-coupling agent, while Structure 20 is another azo dye formed by combining a thiophene diazo component and an arylamine-coupling component.

The thiazine class of dyes is based around a central chromophoric thiazine ring, which is part of a condensed three-ring system whose outer components may be benzene or naphthalene nuclei. Blue thiazine dyes are obtained when auxochromes are introduced meta to the sulfur atom. An example is Methylene Blue (C.I. Basic Blue 9, Structure 21).

Nitro dyes are characterized by the presence of one or more nitro groups conjugated with electron-donor substituents such as hydroxy or amino groups on benzenoid or naphthol rings. Nitro dyes yield mostly hues in the yellow and brown range. An example is 2-amino-5-nitrophenol (Structure 22).

In the present inventors' earlier U.S. Pat. No. 5,688,291, a single-step composition was disclosed, which utilized disperse azo and anthraquinone compounds in category-2 bleach, to simultaneously lighten the hair up to seven levels and deposit different colors. The present invention discloses compositions consisting of other classes of dyes, namely acid and basic colorants containing specific chemical constituents, which are more substantive to hair and deliver enhanced deposit and more vivid colors. These acid and basic colorants belong chemically to the azo, triarylmethane, thiazine, and nitro classes, and can be used in conjunction with a category-2 bleach to lighten hair up to seven levels and deposit bright colors in a single step. They all have the unique property of possessing deactivating or weakly activating groups positioned ortho and/or para to the chromophoric and/or auxochromic centers of the dye molecules.

U.S. Pat. No. 5,474,578, to Chan, issued Dec. 12, 1995, discloses a process for temporary erasable hair coloring. The process utilizes a composition comprising triarylmethane dyes, which are subsequently decolorized or "erased" by reacting them with alkaline hydrogen peroxide. While the patent teaches the use of triarylmetbane dyes in a manner completely opposite to the teachings of the invention disclosed herein, namely by taking advantage of their known instability to alkaline hydrogen peroxide (category-1 bleach), yet the patent teaches in examples 5–7 that some triarylrnethane dyes could not be decolorized by alkaline hydrogen peroxide. As stated above and as those skilled in the art may know, dyes that are stable in category-1 bleach are not necessarily stable in category-2 bleach. To prove the point, dyes specified in examples 5–7 of Chan '578 were tested in the stronger bleach system described below (category-2 bleach). They were all decolorized and found to be unstable.

U.S. Pat. No. 5,232,494, to Miller, issued Aug. 3, 1993, discloses a system consisting of two coloring compositions for inks in markers and the like comprising of a first erasable coloring composition containing polymethine and azo dyes that are decolorized by bleach, and a second coloring composition containing pigments and xanthine dyes that are resistant to chemical attack. Again, as those skilled in the art know, dyes do not behave the same on different substrates. Hair keratin fibers are dramatically different from cellulosic paper fibers. Also the bleach system used with the second coloring composition comprised of agents that are rarely used in the hair care industry to bleach hair, such agents include hydrogen sulfide, sodium hypochlorite, and the preferred agent being sodium sulfite. Hydrogen peroxide was also mentioned but within the confines of a category I bleach system. When the xanthene dyes Acid Red 52 and Acid Red 87, mentioned in Miller '494 to be highly resistant to chemical attack in the erasable ink system, were tested in the bleach system described below, they were found to be unstable.

The advantages of category-2 bleaches with built-in effective colorants are significant. First, a single-step product will significantly reduce the time of the hair lightening and coloring process, a feature that appeals to both, the client and the salon operator. Second, it reduces the chances of scalp irritation due to prolonged contact of the skin with reactive chemicals (alkalinity, peroxide, oxidation dyes) in traditional two-step applications. And third, the single-step application significantly reduces the damage to the hair because it eliminates the need for additional chemical treatments.

SUMMARY OF THE INVENTION

In accordance with the present invention, there is provided a single-step process and composition of category-2 (persulfate-based) hair bleach, which can simultaneously lighten the hair up to seven levels and effectively deposit various shades of color. This is achieved by including in the bleach composition derivatives of azo, triarylmethane, thiazine, or nitro dyes, which the present invention has identified to be stable in the bleach. Unexpectedly, the present invention has found that only dyes with certain types of chemical groups, situated at specific sites in the dye molecules confer bleach stability on these dyes. It is revealed herein that when linked at the ortho- and/or para-positions relative to the chromophoric centers and auxochrome groups located on or attached to the aromatic rings of these dyes, deactivating or weakly activating chemical groups enhance the survival of these dyes in the alkaline bleach medium. On the contrary, absence of ortho and/or para positioned deactivating or weakly-activating substituents, or presence of strongly activating groups in these positions render the dye molecule susceptible to attack by the bleach and the eventual destruction of these dyes. These deactivating and protective chemical groups may be nitro, halogen, cyano, carboxyl, sulfonic, alkyl or aromatic groups, but not amino, hydroxy, alkoxy or alkylamide groups. These and other objects of the invention will be evident when viewed in light of the detailed description and appended claims.

BRIEF DESCRIPTION OF THE DRAWINGS

The accompanying drawings sheets illustrate the chemical structures of the known dyes, using the structure numbers in the text.

DETAILED DESCRIPTION OF THE PREFERRED EMBODIMENT

Figure 1A:
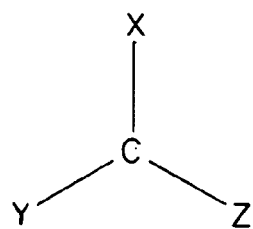
FIG. 1A is an illustration of the chemical structures of structure numbers 1–6.
Figure 1A:
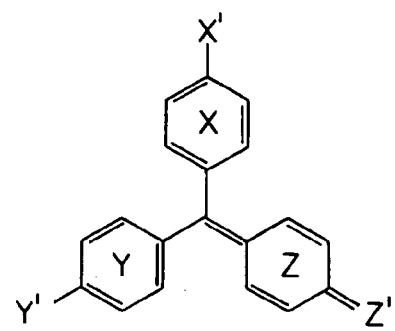
Figure 1A:
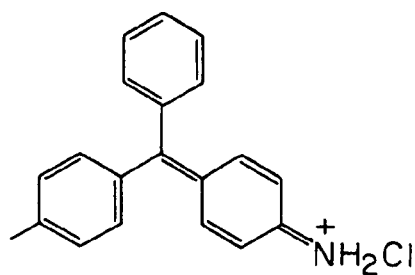
Figure 1A:
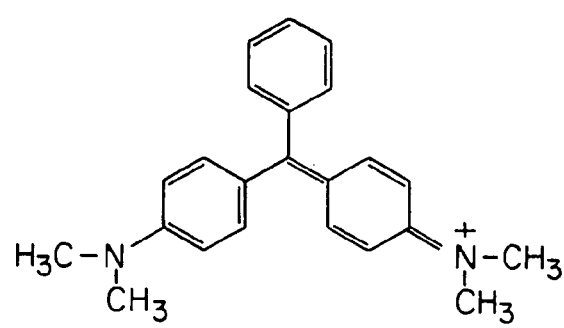
Figure 1A:
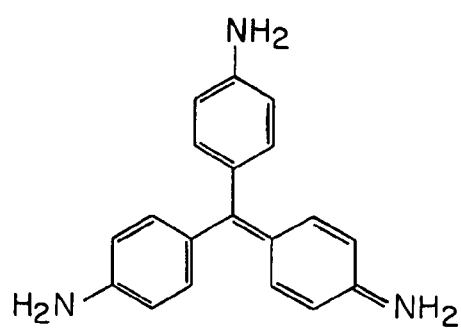
Figure 1A:
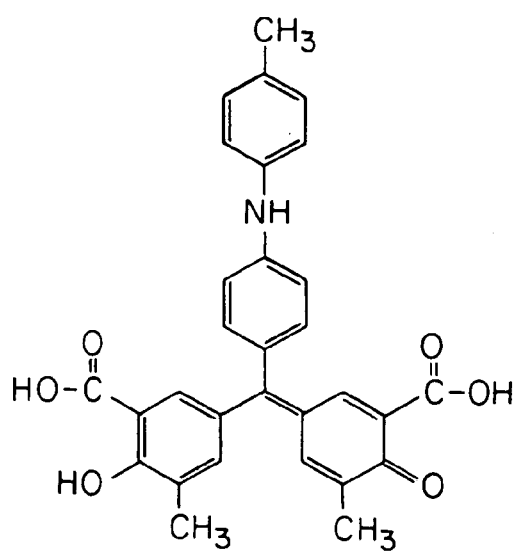
Figure 1B:
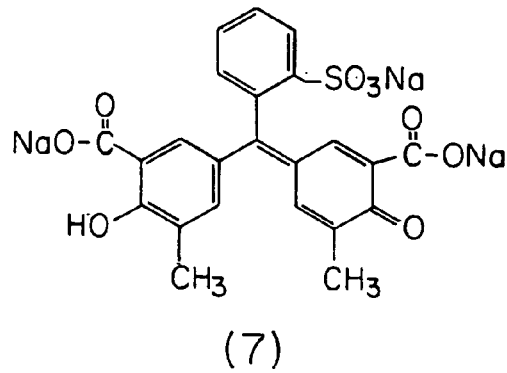
FIG. 1B is an illustration of the chemical structures of structure numbers 7–15.
Figure 1B:
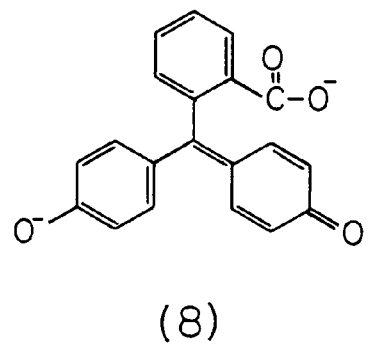
Figure 1B:
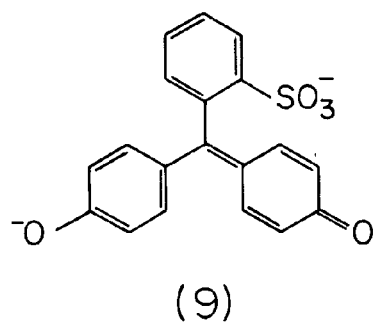
Figure 1B:
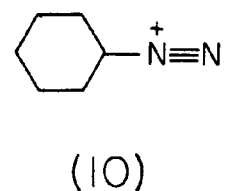
Figure 1B:
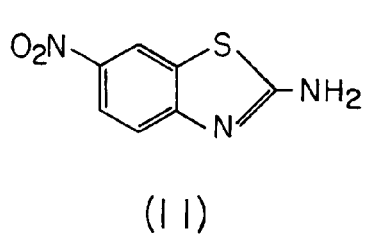
Figure 1B:
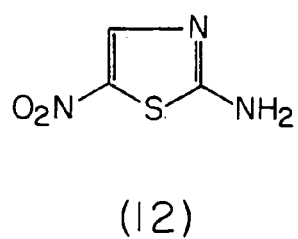
Figure 1B:
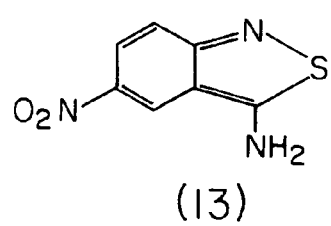
Figure 1B:
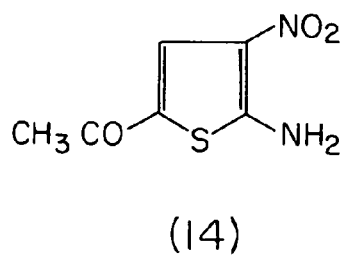
Figure 1B:
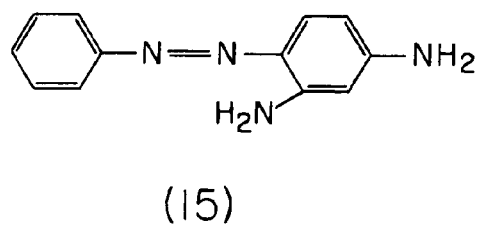
Figure 1C:
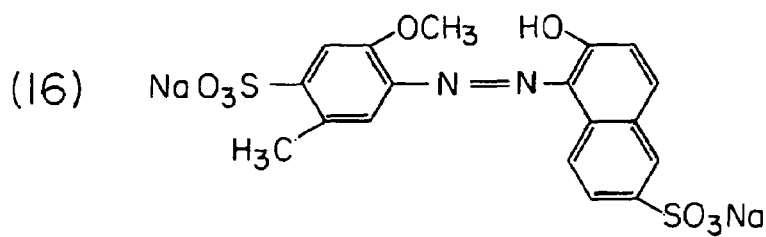
FIG. 1C is an illustration of the chemical structures of structure numbers 16–22.
Figure 1C:
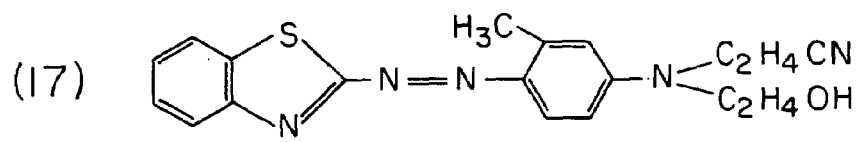
Figure 1C:
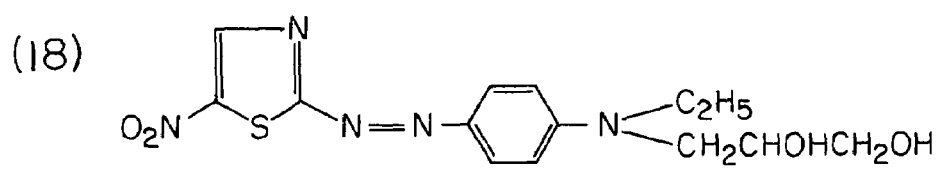
Figure 1C:
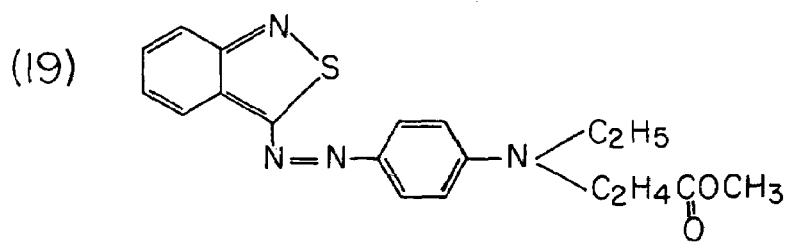
Figure 1C:
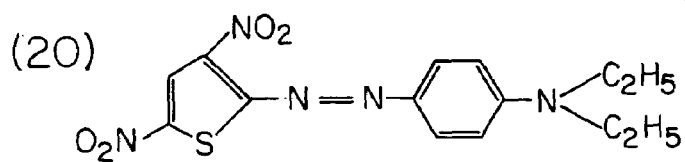
Figure 1C:
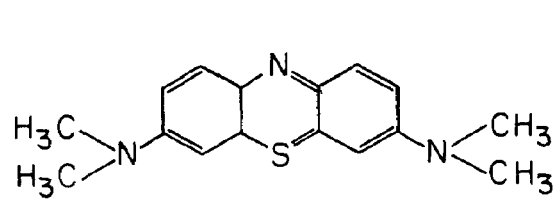
Figure 1C:
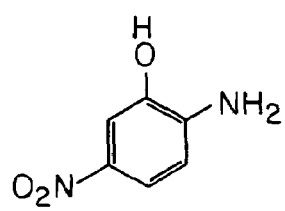
Figure 1D:
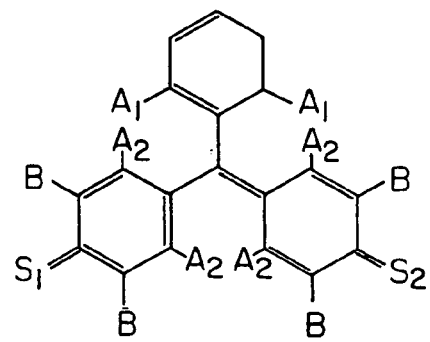
FIG. 1D is an illustration of the chemical structures of structure numbers 23–26.
Figure 1D:
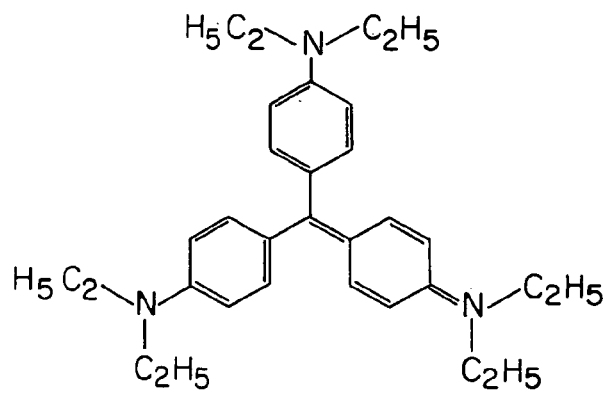
Figure 1D:
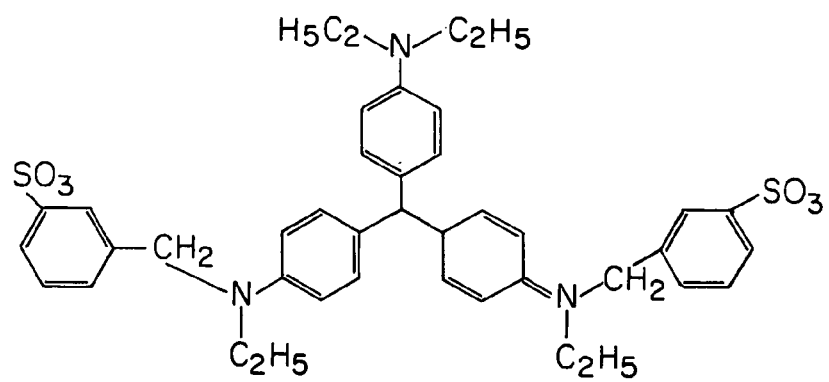
Figure 1D:
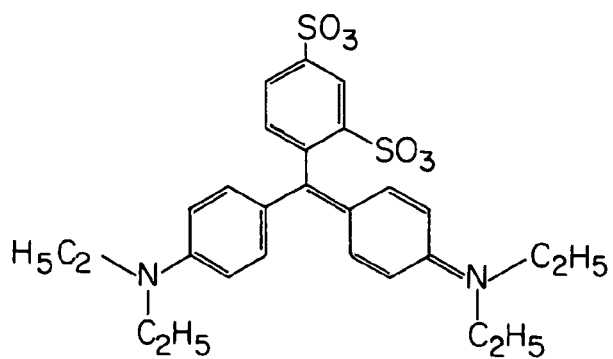
Figure 1E:
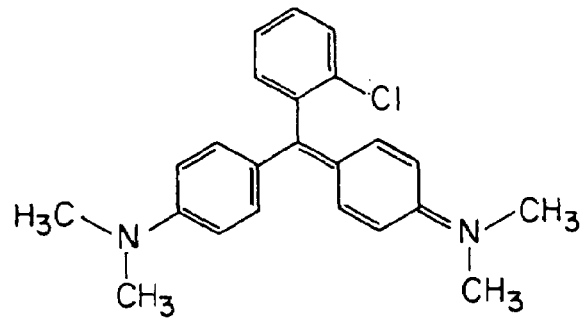
FIG. 1E is an illustration of the chemical structures of structure numbers 27–30.
Figure 1E:
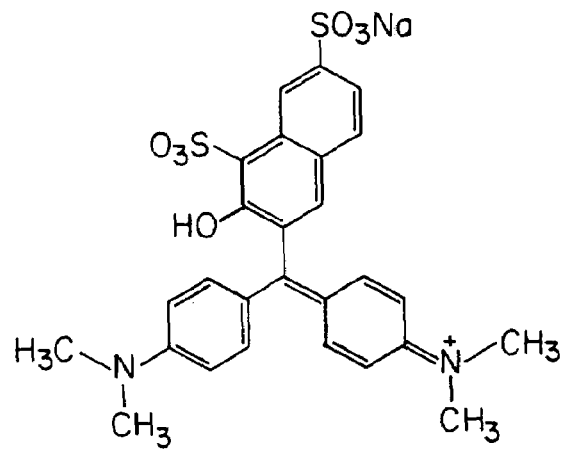
Figure 1E:
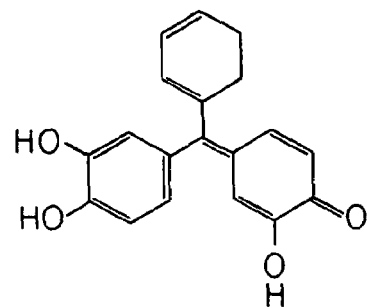
Figure 1E:
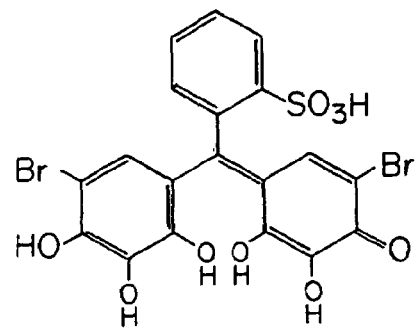
Figure 1F:
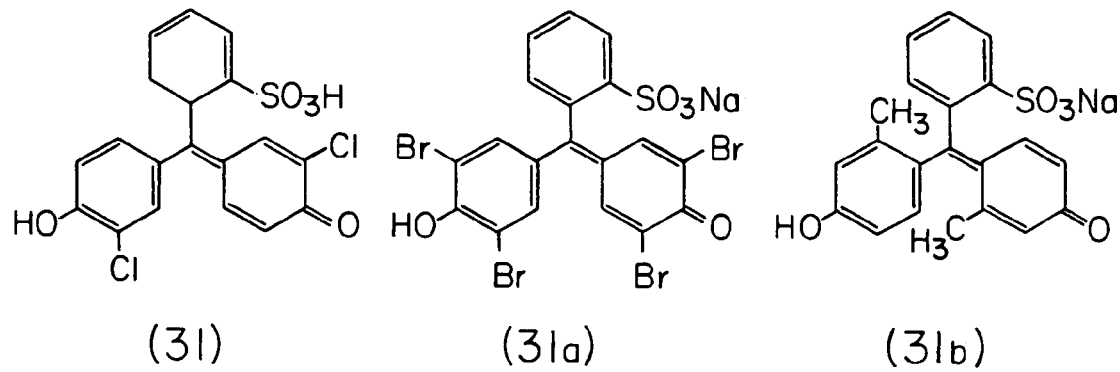
FIG. 1F is an illustration of the chemical structures of structure numbers 31–35.
Figure 1F:
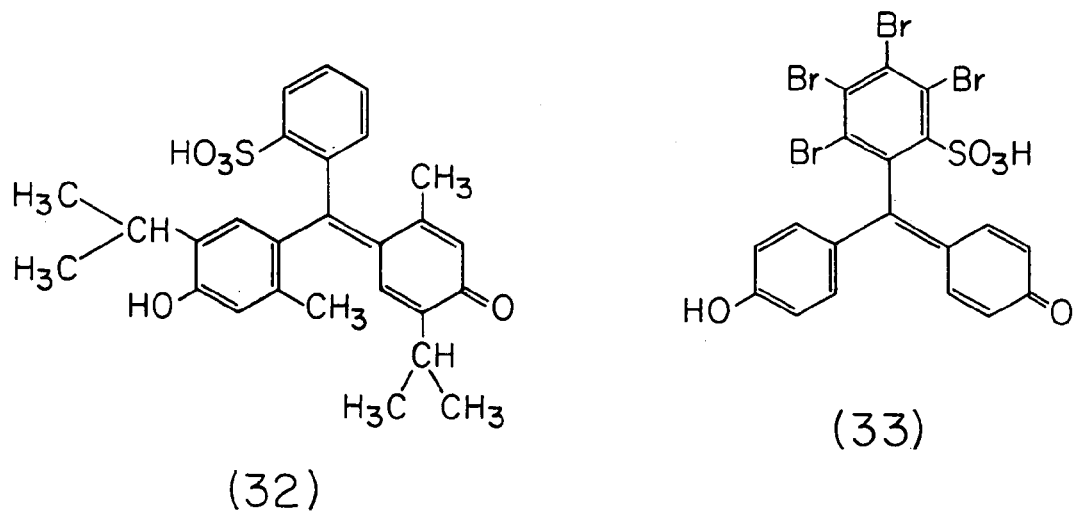
Figure 1F:
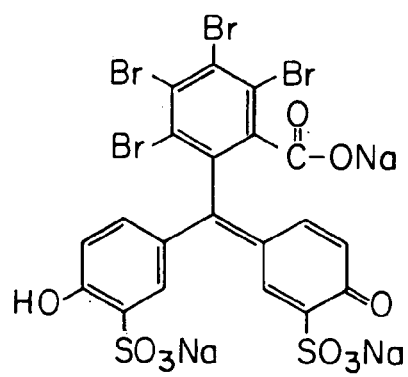
Figure 1F:
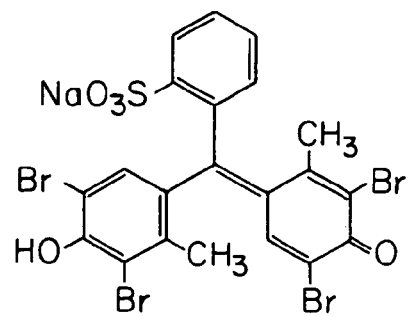
Figure 1G:
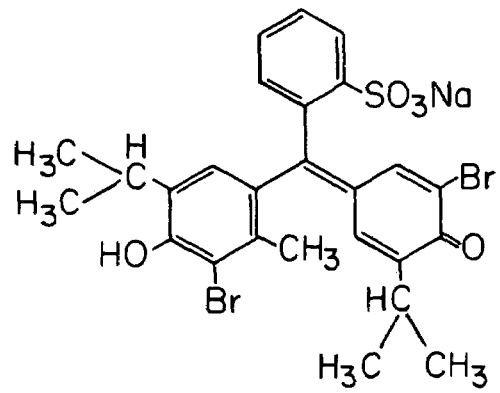
FIG. 1G is an illustration of the chemical structures of structure numbers 36–40.
Figure 1G:
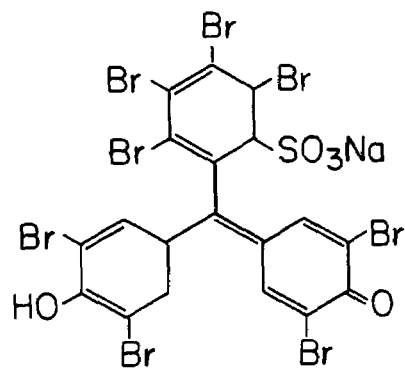
Figure 1G:
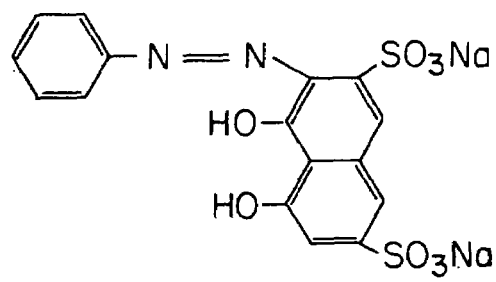
Figure 1G:
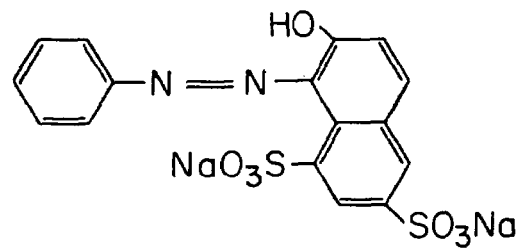
Figure 1H:
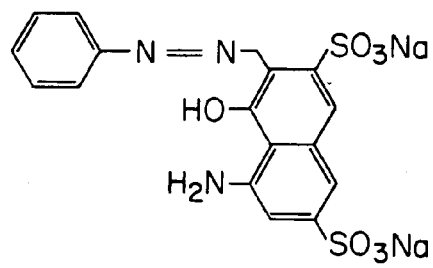
FIG. 1H is an illustration of the chemical structures of structure numbers 41–45.
Figure 1H:
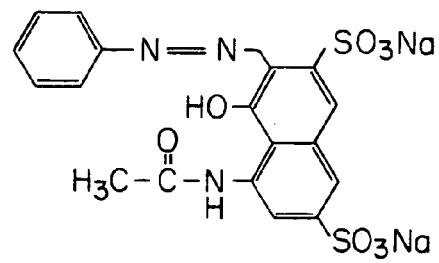
Figure 1H:
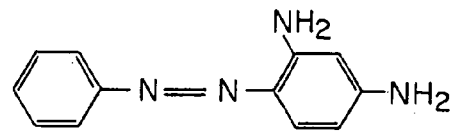
Figure 1H:
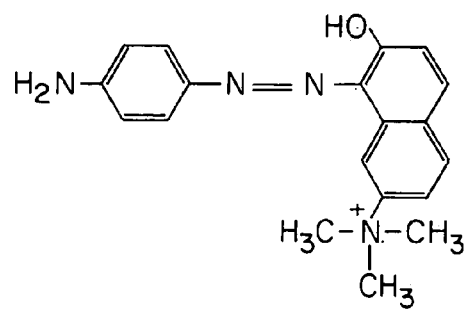
Figure 1H:
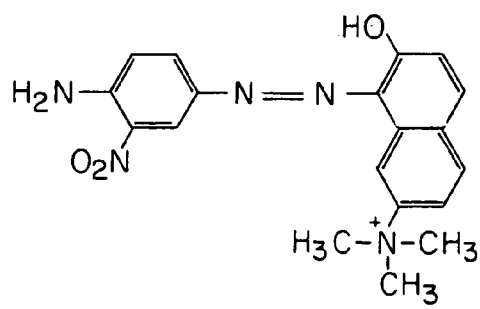
Figure 1I:
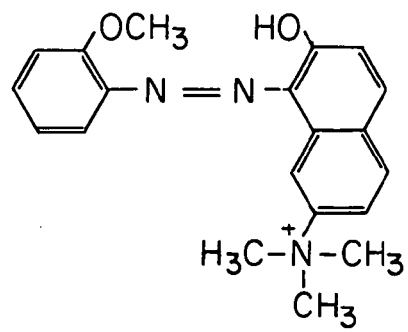
FIG. 1I is an illustration of the chemical structures of structure numbers 46–49.
Figure 1I:
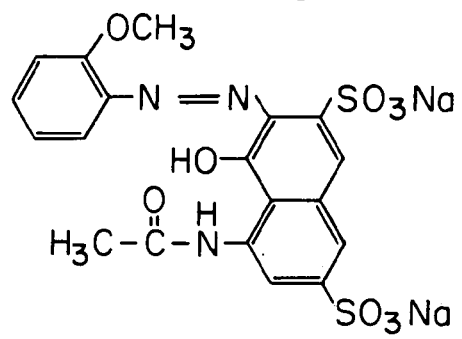
Figure 1I:
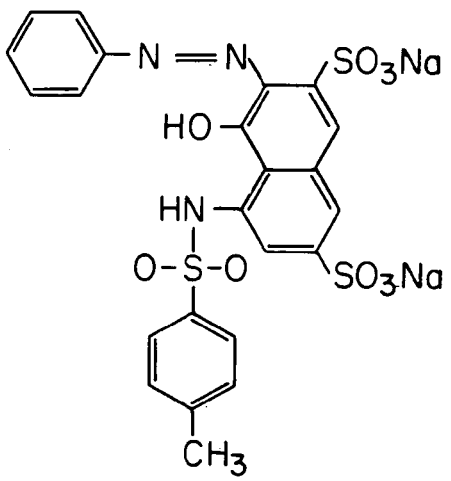
Figure 1I:
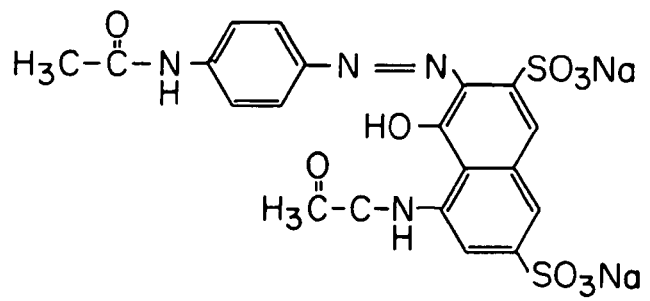
Figure 1J:
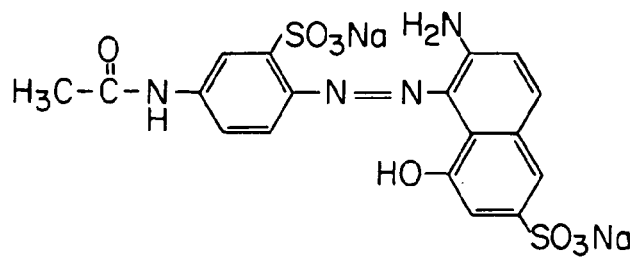
FIG. 1J is an illustration of the chemical structures of structure numbers 50–56.
Figure 1J:
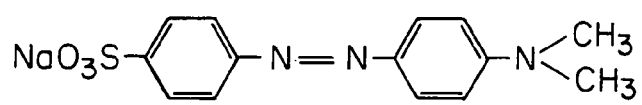
Figure 1J:
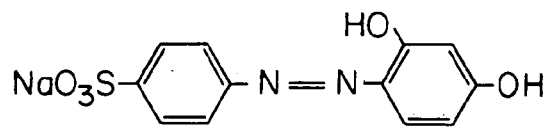
Figure 1J:
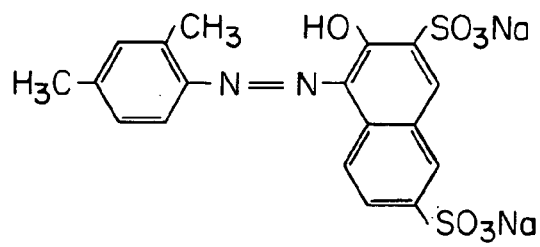
Figure 1J:
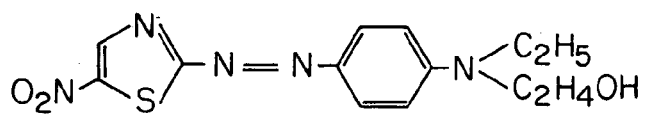
Figure 1J:
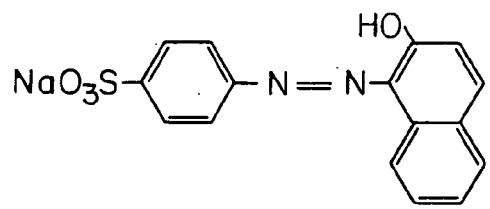
Figure 1J:
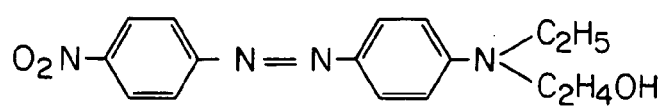
Figure 1K:
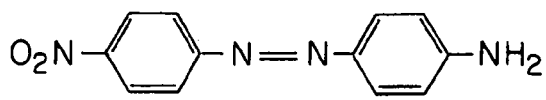
FIG. 1K is an illustration of the chemical structures of structure numbers 57–63.
Figure 1K:
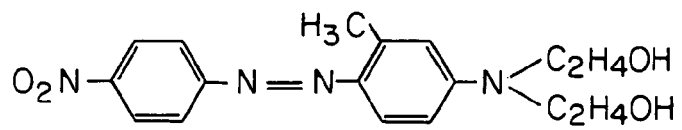
Figure 1K:
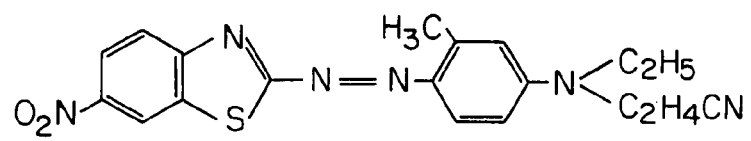
Figure 1K:
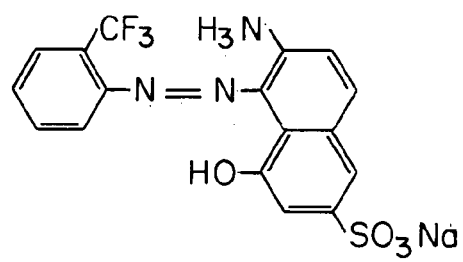
Figure 1K:
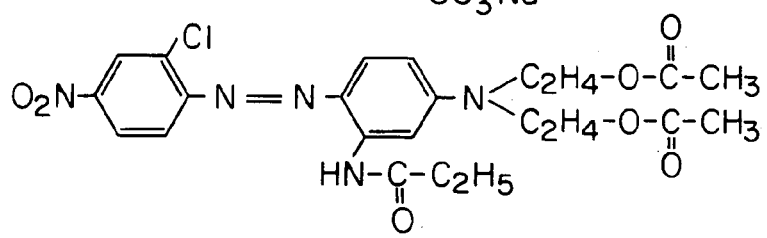
Figure 1K:
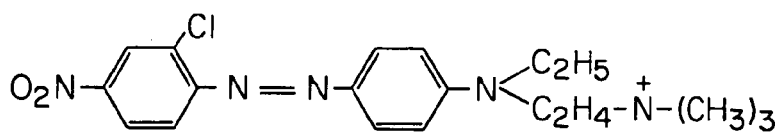
Figure 1K:
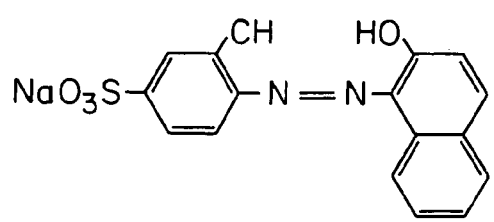
Figure 1L:
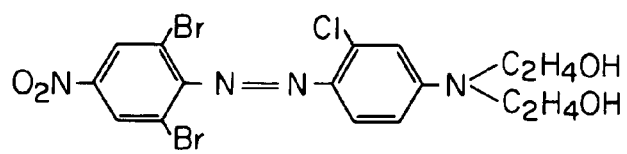
FIG. 1L is an illustration of the chemical structures of structure numbers 64–76.
Figure 1L:
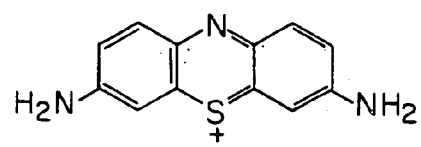
Figure 1L:
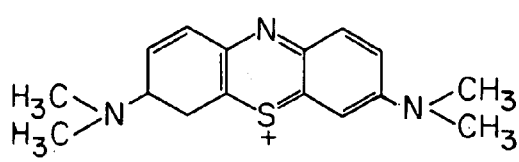
Figure 1L:
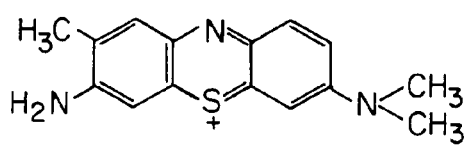
Figure 1L:
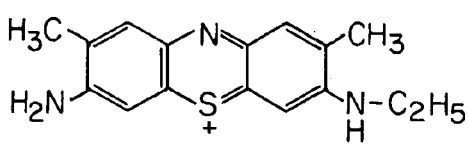
Figure 1L:
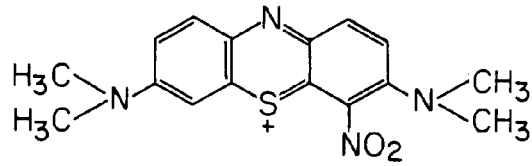
Figure 1L:
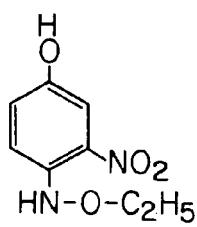
Figure 1L:
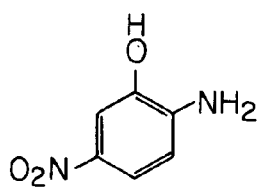
Figure 1L:
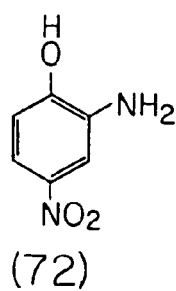
Figure 1L:
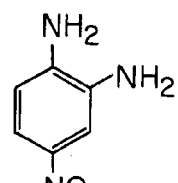
Figure 1L:
Figure 1L:
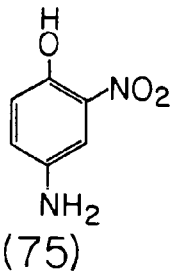
Figure 1L:
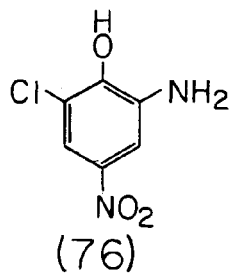
Figure 1M:
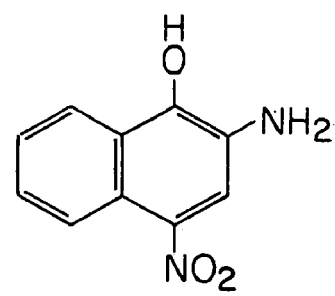
FIG. 1M is an illustration of the chemical structures of structure numbers 77–78.
Figure 1M:
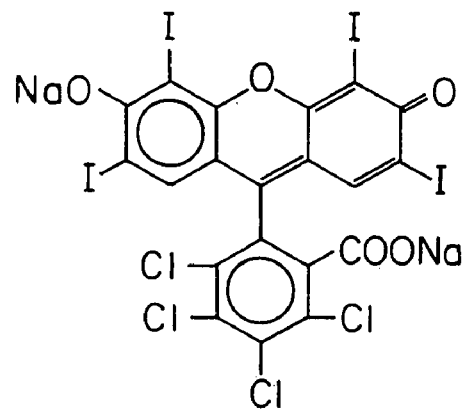

The best mode for carrying out the invention will now be described, and this description is not meant to limit the invention, as measured by the scope and spirit of the claims. To achieve the object of the present invention, namely creating single-step bleach that lightens the hair by more than f(our levels while at the same time adding color to it, hundreds of colorants belonging to the triarylmethane, azo, thiazine and nitro classes of dyes were tested for three properties: 1) stability in a medium of category-2 bleach; 2) ability to color the hair; and 3) longevity of the deposited color.

The testing procedure, which was employed to screen these dyes, consisted of three steps: First, the dye to be tested was incorporated at a concentration of 1% by weight into the bleach powder shown in Table 1. This dye concentration was selected arbitrarily and is not meant to limit the practical application range of the dyes. Bleach-stable dyes may be used at concentrations of less than 0.01%. Twenty grams of the dye-bleach powder blend were mixed in a plastic bowl with 40 gram s of 12% hydrogen peroxide solution. The mixture took on the color of the dye used. Using a brush, the bleach mixture was applied to natural white and medium brown human hair swatches, wrapped in aluminum foil, and incubated in an oven at 45° C. (simulating the action of a hair dryer) for 10 minutes. The remaining mixture in the bowl was monitored for any change in color associated with instability. Second, if the oven-processed hair swatches revealed significant color deposit, and if no appreciable color breakdown was noticed in both the foil and the bowl, then another set of swatches would be treated with the same bowl mixture which is left to age for at least 30 minutes on the bench. This is intended to simulate the average time required to complete a normal bleach application by an experienced user. The second set thus obtained should achieve about the same level of color deposit, as did the first, in order for the dye to be deemed acceptable. Third, once a dye has been judged acceptable in terms of color deposit and stability in bleach, it would be assessed for durability of color under repeated washing. This was achieved by subjecting the treated swatches to ten cycles of shampooing and drying. A color is deemed satisfactory if it retained over 50% of the original color intensity after 10 cycles of washing.

TABLE 1

Composition of Bleach Powder Used as Category-2 Bleach Medium for Assaying Dye Stability.

| Ingredient | % composition |
|---|---|
| Ammonium Persulfate | 30.0 |
| Potassium Persulfate | 20.0 |
| Sodium Silicate | 24.0 |
| Magnesium Oxide | 12.0 |
| Hydroxethylcellulose | 5.0 |
| Soap Beads | 6.0 |
| Silica | 2.0 |
| Dye | 1.0 |

TABLE 1-continued

The greatest majority of the dyes tested, not surprisingly, failed at least one of the criteria listed above. Efforts to create a single-step full action bleach and colorant have been going on for decades with very limited success. The end result invariably had been the same: Dyes that performed well in category-1 bleach medium, failed in category-2 bleach medium.

The present invention has identified a small number of colorants that performed very well in a category-2 bleach system. These colorants belong to four dye chemical classes: Triarylmethane, azo, thiazine and nitro dyes. The surprising discovery resulting from these extensive studies is that all dyes found to be stable in the bleach under the conditions outlined above have a common feature namely, the presence of certain chemical substituents on the aromatic rings in the ortho or para positions relative to the constituents of the chromophoric system of these dyes (azo group of azo dyes, central methane carbon and terminal para-positioned auxochromes of triarylmethane dyes, conjugated nitrogen and sulfuir atoms of the thiazine ring of thiazine dyes, and the conjugated nitro-hydroxy or nitro-amino groups of nitro dyes). These chemical constituents are also those that exert a deactivating or only weakly activating influence on aromatic rings to which they are attached. None were of the strongly activating species such as amino, hydroxy, alkoxy or alkylamide groups. The deactivating groups include, nitro, halide, cyano, carboxyl and sulfonic groups, while the weakly activating groups include alkyl and aryl groups. These ortho- or para-positioned groups, depending on their type protect the chromophoric components against the strong oxidative environment of the bleach.

Without limiting this disclosure to any theory, it is possible that the protection of the chromophores by these groups is due to several factors, which include: site deactivation rendering the vicinity of the chromophores much less reactive, combined with meta-directive effects of these meta-directing groups so that attacking groups are directed away from their ortho neighbors. In addition, steric effects may play a role such as may be the case with weakly activating groups. Here the mere presence of a benign group may physically shield the chromophore from chemical attack.

Another unexpected finding resulting from these studies is that for triarylmethane bleach-stable dyes, the auxochrome-void meso ring contributed by an aromatic aldehyde or aromatic amhydride during the trial initial synthetic steps, plays a critical role in conferring bleach stability on these dyes. The substitution of this ring with deactivating (electron-withdrawing) or weakly activating groups at the ortho positions relative to the central carbon is a necessary requirement for stability of the dyes in any bleach system. As the number of substituents on the triarylmethane rings (particularly the meso ring) increases, so does the stability of the dyes in the bleach. The triarylmethanes can theoretically have up to six substituents (assuming there are no steric limitations) positioned ortho to the central carbon atom on three surrounding rings. For sake of clarity in interpreting the data, ortho substituents positioned on the meso ring are labeled $A_1$ stubtituents while those positioned on both auxochromic rings are labeled $A_2$ (structure 23). There can be also up to four ortho substituents, labeled B, located ortho to auxochromes $S_1$ and $S_2$. Auxochromes $S_1$ and $S_2$ are either amino or hydroxy groups and can be either identical or different. In more complex triarylmethane dyes, additional aromatic rings that are part of a tertiary amino auxochrome may provide also ortho substituents to that auxochrome.

Table 2 lists several triarylmethane dyes, showing the relationship between dye stability in the bleach and the number and location of ortho substituents of the whole chromophoric system. Testing of these dyes was performed with the bleach powder composition listed in Table 1, in accordance with the procedure outlined above. Evaluation of stability was done subjectively, and stability ratings were based on a scale of zero to ten, with ten being excellent stability (color persisting for over one hour in the bleach with minimal breakdown), and zero being immediate breakdown and disappearance of color. A stability rating below 5 chromes and two $A_1$-substituents protecting its central carbon atom is more stable than one having only two B-substituents and two $A_1$-substituent (Compare Structures 34 and 38 for example). No stable dyes void of any $A_1$-substituents were found. Dyes with only two $A_1$-substituents were marginally stable but their stability is significantly enhanced by B-substituents (Structures 33 and 34). Dyes with no A- or B-substituents were not stable at all. $A_2$-substituents appear to play only a supporting role to $A_1$-substituents (compare for example Structures 31a and 34). As more and more groups are added to the rings, stability increases proportionally, so that dyes with the most substituents on all three aromatic rings are the most stable. For example, Tetrabromophenol Blue (Structure 38) with its meso ring fully substituted with deactivating groups and contributing stabilization to the central carbon from both ortho positions as well as the para position, is a very stable dye.

Whereas alkyl, carboxy, halide, sulfonic, and nitro substituents enhance triarylmethane dye stability in bleach, ortho-hydroxy (—OH) substituents were found to reduce stability of these dyes and hasten their decomposition in the bleach (compare Structures 30 and 35)

TABLE 2

Stability of some triarylmethane dyes in category-2 bleach in relation to the number of substituents positioned ortho to the chromophoric centers of these dyes.

| Dye Name | CI No. | CAS No. | # Of Ortho-Substituents $A_1$ | $A_2$ | B | Stability Rating | Structure |
|---|---|---|---|---|---|---|---|
| CI Basic Green 4 | 42000 | 569-64-2 | 0 | 0 | 0 | 0 | 4 |
| CI Basic Red 9 | 42500 | 569-61-9 | 0 | 0 | 0 | 0 | 5 |
| CI Basic Violet 4 | 42600 | 2390-59-2 | 0 | 0 | 0 | 0 | 24 |
| CI Acid Violet 17 | 42650 | 4129-84-4 | 0 | 0 | 0 | 0 | 25 |
| Phenolphthalein | | 77-09-8 | 1 | 0 | 0 | 0 | 8 |
| Phenol Red | | 143-74-8 | 1 | 0 | 0 | 0 | 9 |
| CI Acid Blue 1 | 42045 | 129-17-9 | 1 | 0 | 0 | 0 | 26 |
| CI Basic Blue 1 | 42025 | | 1 | 0 | 0 | 0 | 27 |
| CI Acid Green 50 | 44090 | 3087-16-9 | 1 | 0 | 0 | 0 | 28 |
| Pyrocatechol Violet | | 115-41-3 | 1 | 0 | 2* | 0 | 29 |
| Bromopyrogallol Red | | 16574-43-9 | 1 | 2* | 4* | 0 | 30 |
| Chlorophenol Red | | 4430-20-0 | 1 | 0 | 2 | 1 | 31 |
| Bromophenol Blue 3',3'',5',5''-Tetrabromo-sulfonephthalein | | 115-39-9 | 1 | 0 | 4 | 1 | 31a |
| m-Cresolsulfonephthalein | | 2303-01-7 | 1 | 2 | 0 | 2 | 31b |
| Thymol Blue | | 62625-21-2 | 1 | 2 | 2 | 2 | 32 |
| 3,4,5,6-Tetrabromophenol-sulfonephthalein | | 123333-63-1 | 2 | 0 | 0 | 5 | 33 |
| Sulfobromophthalein | | 123359-42-2 | 2 | 0 | 2 | 6 | 34 |
| Bromocresol Green | | 62625-32-5 | 1 | 2 | 4 | 7 | 35 |
| Bromothymol Blue | | 76-59-5 | 1 | 2 | 4 | 7 | 36 |
| Tetrabromophenol Blue (2,3,4,5,3',3'',5',5''-octabromo-phenolsulfonphthalein) | | 4430-25-5 | 2 | 0 | 4 | 9 | 38 |

Substituents marked by (*) are hydroxy groups, which are both activating and destabilizing means that the dye is not useful as a colorant in such a bleach system. A rating of 5 or above means that the dye may be used with the bleach system. Dyes are listed by their Color Index names and numbers when available, or by their trade names and CAS numbers.

As can be concluded from the data of Table 2, stability of triarylmethane dyes depends on the number, type and location of ortho substituents. Stability of a dye increases with the number of these ortho substituents. For example, a dye, which has four B-substituents protecting both of its auxo- Tables 3 through 5 show test results of azo, thiazine and nitro dyes, respectively. For azo dyes, the major factor in determining dye stability is the substitution profile of the diazo component. Substitution of the coupling component plays minor role in this regard, and mostly in situations where an ortho hydroxy group is in a position to form hydrogen bonding with the adjacent azo group. Deactivating groups on the diazo component located ortho or para to the azo bond enhance dye stability while activating groups or absence of any groups render azo dyes highly susceptible to bleach attack (see structures 39 to 49). Of the deactivating groups, the nitro group is the strongest and most effective in this regard. Weakly activating groups, such as the methyl group, are slightly effective when located in the ortho position but can augment the action of weak deactivating substituents like the sulfonic group placed in the para position (compare structures 55 and 63). As was observed with the meso ring of the triarylmethanes, increasing the number of electron-withdrawing substituents on, the diazo component enhances stability further (Structure 64).

possibly because the balance of the substituent groups favors the activating and de-stabilizing groups. It is an established fact in organic chemistry that when a strongly activating amino or hydroxy group competes with a strongly deactivating nitro group on the same aromatic ring, the activating group determines the order of substitution. Of course when more than one activating group is present on the same ring, the de-stabilizing effect becomes more pronounced. This has been the case with the great majority of nitro dyes (Structures 70 through 76). The very few dyes that were found to

TABLE 3

Stability of some azo dyes in category-2 bleach based on nature of substituents of the diazo component in relation to the azo bond.

| Dye Name | CI No. | Group(s) | position | Stability Rating | Structure |
| --- | --- | --- | --- | --- | --- |
| Acid Red 29 | 16570 | None | None | 1 | 39 |
| Acid Orange 10 | 16230 | None | None | 1 | 40 |
| Acid Red 33 | 17200 | None | None | 1 | 41 |
| Acid Red 1 | 18050 | None | None | 1 | 42 |
| Basic Orange 2 | 11270 | None | None | 1 | 43 |
| Basic Brown 16 | 12550 | Amino | para | 1 | 44 |
| Basic Brown 17 | 12251 | Amino, Nitro | para, meta | 1 | 45 |
| Basic Red 76 | 12245 | Methoxy | ortho | 1 | 46 |
| Acid Violet 12 | 18075 | Methoxy | ortho | 1 | 47 |
| Acid Violet 5 | 18125 | Alkylamide | para | 1 | 48 |
| Acid Violet 7 | 18055 | Alkylamide | para | 1 | 49 |
| Acid Red 37 | 17045 | Alkylamide, sulfonic | para, ortho | 3 | 50 |
| Acid Orange 52 | 13025 | Sulfonic | para | 3 | 51 |
| Acid Orange 6 | 14270 | Sulfonic | para | 3 | 52 |
| Acid Red 26 | 16150 | methyl, methyl | para, ortho | 5 | 53 |
| Disperse Blue 106 | 111935 | Nitro | heterocyclic ring | 6 | 54 |
| Acid Orange 7 | 15510 | Sulfonic | para | 6 | 55 |
| Disperse Red 1 | 1110 | Nitro | para | 7 | 56 |
| Disperse Orange 3 | 11005 | Nitro | para | 7 | 57 |
| Disperse Red 17 | 11210 | Nitro | para | 7 | 58 |
| Disperse Red 179 | 112290 | Nitro | heterocyclic ring | 8 | 59 |
| Disperse Blue 148 | 11124 | Nitro | heterocyclic ring | 8 | 19 |
| Acid Red 337 | 17102 | Trifluromethyl | ortho | 8 | 60 |
| Disperse Red 167 | 11338 | Nitro, Chloro | para, ortho | 8 | 61 |
| Basic Red 18 | 11085 | Nitro, Chloro | para, ortho | 8 | 62 |
| Acid Orange 8 | 15575 | Sulfonic, methyl | para, ortho | 8 | 63 |
| Disperse Red 118 | 11152:2 | Nitro, bromo, bromo | para, ortho, ortho | 9 | 64 |

Because thiazine dyes are relatively few in number, only a handful of dyes were available for testing. The thiazine ring itself seems to be more resistant to chemical attack than unprotected triaryl or azo counterparts, possibly due to the condensed ring arrangement. Nonetheless, ortho substitution relative to the auxochromes enhances dye stability as shown in Table 4.

TABLE 4

Effect of substituents on stability of some thiazine dyes in category-2 bleach.

| Dye Name | CI No. | Group(s) | position | Stability Rating | Structure |
| --- | --- | --- | --- | --- | --- |
| Thionin | 52000 | None | None | 5 | 65 |
| Basic Blue 9 | 52015 | None | None | 5 | 66 |
| Basic Blue 17 | 52040 | Methyl | ortho | 6 | 67 |
| Basic Blue 24 | 52030 | Methyl, Methyl | ortho, ortho | 7 | 68 |
| Basic Green 5 | 52020 | Nitro | ortho | 7 | 69 |

As mentioned above, the chromophore of the nitro class of dyes is a result of the presence of one or more nitro groups conjugated with one or more hydroxy or amino groups. The majority of the dyes tested (Table 5) were unstable to bleach be stable are those whose constituent balance favors the deactivating nitro dyes. Structures 77 and 78 for example, contain two deactivating nitro groups and only one activating hydroxy group per molecule. One of the nitro groups is ortho and the other one is para relative to the hydroxy group.

TABLE 5

Effect of substituents on stability of some nitro dyes in category-2 bleach.

| Dye Name Structure | Group(s) | position | Stability Rating | |
| --- | --- | --- | --- | --- |
| 4-hydroxyethanolamino-3-nitrophenol | Nitro, hyroxyethanolamino | meta, para | 0 | 70 |
| 2-amino-5-nitrophenol | hydroxy, Amino, Nitro | ortho, meta | 1 | 71 |
| 2-amino-4-nitrophenol | hydroxy, Amino, Nitro | ortho, para | 2 | 72 |
| 4-nitro-o-phenylenediamine | Amino, Amino, Nitro | ortho, para | 2 | 73 |
| 2-nitro-p-phenylenediamine | Amino, Nitro, Amino | ortho, para | 2 | 74 |
| 4-amino-2-nitrophenol | hydroxy, Nitro, Amino | ortho, para | 2 | 75 |

TABLE 5-continued

Effect of substituents on stability of some nitro dyes in category-2 bleach.

| Dye Name Structure | Group(s) | position | Stability Rating | |
|---|---|---|---|---|
| 2-amino-6-chloro-4-nitrophenol | Hydroxy, Amino, Nitro, Chloro | ortho, para, ortho | 4 | 76 |
| Acid Yellow 24 | Hydroxy, Nitro, Nitro | ortho, para | 9 | 77 |

In what follows, specific examples will be cited to illustrate the applicability of the present invention.

EXAMPLE 1

A formulation containing a triarylmethane dye is provided for coloring brown hair blue in a single step. A powder having the composition:

| | % By Weight |
|---|---|
| Bleach composition of Table 1 | 98.0 |
| Tetrabromophenol Blue (4430-25-5) | 2.0 | was mixed in the ratio of 1:2 with 12% hydrogen peroxide solution (1 part powder: 2 parts peroxide) to yield a smooth cream, applied to natural brown human hair swatches, then wrapped in aluminum foil, and placed in an oven at 45° C. for 15 minutes. Result: Hair was lightened and colored a royal blue shade.

EXAMPLE 2

A formulation containing a triarylmethane dye is provided for coloring brown hair violet in a single step. A powder having the composition:

| | % By Weight |
|---|---|
| Bleach composition of Table 1 | 98.0 |
| Tetrabromophenol Blue (4430-25-5) | 1.5 |
| Acid Red 94 (632-69-9) | 0.5 | was prepared and applied in the same procedure of Example 1. Result: Hair was lightened and colored violet. Acid Red 94 is a fluorone dye (CI #45440), which has the common name Rose Bengal. It is also used in several other examples below. A structure of Acid Red 94 is provided as Structure 78.

EXAMPLE 3

A formulation containing triarylmethane is provided to color brown hair purple in a single step. A powder having the composition

| | % By Weight |
|---|---|
| Bleach composition of Table 1 | 98.0 |
| Acid Red 94 (632-69-9) | 1.0 |
| Bromocresol Green (62625-32-5) | 1.0 | was prepared and applied in the same procedure of Example 1. Result: Hair was lightened and colored purple.

EXAMPLE 4

A formulation containing triarylmethane dye and nitro dye is provided to color brown hair green in a single step. A powder having the composition

| | % By Weight |
|---|---|
| Bleach composition of Table 1 | 98.5 |
| Basic Blue 77 | 1.0 |
| Acid Yellow 24 (605-69-6) | 0.5 | was prepared and applied in the same procedure of Example 1. Result: Hair was lightened and colored green. The Basic Blue 77 dye is also a triarylmethane dye sold commercially under the trade name SEVRON.

EXAMPLE 5

A formulation containing an azo dye and a nitro dye is provided to color brown hair gold red in a single step. A powder having the composition

| | % By Weight |
|---|---|
| Bleach composition of Table 1 | 98.0 |
| Acid Red 94 (632-69-9) | 1.0 |
| Acid Orange 8 (5850-86-2) | 0.8 |
| Acid Yellow 24 (605-69-6) | 0.2 | was prepared and applied in the same procedure of Example 1. Result: Hair was lightened and colored gold red.

EXAMPLE 6

A formulation containing the same dyes as in Example 5, but in different proportions, is provided to color brown hair orange in a single step. A powder having the composition

| | % By Weight |
|---|---|
| Bleach composition of Table 1 | 98.0 |
| Acid Red 94 (632-69-9) | 0.3 |
| Acid Orange 8 (5850-86-2) | 1.0 |
| Acid Yellow 24 (605-69-6) | 0.7 | was prepared and applied in the same procedure of Example 1. Result: Hair was lightened and colored orange.

EXAMPLE 7

A formulation containing an azo and a thiazine dye is provided to color brown hair copper red in a single step. A powder having the composition

| | % By Weight |
|---|---|
| Bleach composition of Table 1 | 97.5 |
| Acid Red 94 (632-69-9) | 1.0 |
| Acid Orange 8 (5850-86-2) | 1.0 |
| Basic Blue 24 (6586-05-6) | 0.5 | was prepared and applied in the same procedure of Example 1. Result: Hair was lightened and colored copper red.

EXAMPLE 8

A formulation containing a nitro dye is provided to color brown hair yellow in a single step. A powder having the composition

|  | % By Weight |
| --- | --- |
| Bleach composition of Table 1 | 99.0 |
| Acid Yellow 24 (605-69-6) | 1.0 | was prepared and applied in the same procedure of Example 1. Result: Hair was lightened and colored yellow.

EXAMPLE 9

A formulation containing a nitro and a triarylmethane dye is provided to color black hair dark blonde in a single step. A powder having the composition

|  | % By Weight |
| --- | --- |
| Bleach composition of Table 1 | 99.0 |
| Tetrabromophenol Blue (4430-25-5) | 0.4 |
| Acid Red 94 (632-69-9) | 0.4 |
| Acid Yellow 24 (605-69-6) | 0.2 | was prepared and applied in the same procedure of Example 1. Result: Hair was lightened and colored dark blonde.

EXAMPLE 10

A formulation containing the same dyes as in Example 9, but in different proportions, is provided to color brown hair platinum blonde in a single step. A powder having the composition

|  | % By Weight |
| --- | --- |
| Bleach composition of Table 1 | 98.0 |
| Tetrabromophenol Blue (4430-25-5) | 0.2 |
| Acid Red 94 (632-69-9) | 0.2 |
| Acid Yellow 24 (605-69-6) | 0.1 | was prepared and applied in the same procedure of Example 1. Result: Hair was lightened and colored platinum blonde.

What is claimed is:

1. A composition for simultaneously lightening and coloring hair, said composition comprising:
    a category-2 bleach; and
    a dye selected from the group consisting of acid dyes belonging to the azo, triarylmethane, thiazine and nitro chemical classes and basic dyes belonging to the triarylmethane, thiazine and nitro chemical classes, the molecules thereof having at least one chromophore, the dye being stable in the category-2 bleach.

2. The composition of claim 1, wherein the dye molecules further comprise at least one auxochrome.

3. The composition of claim 1, wherein the dye has at least one deactivating group positioned ortho or para to the chromophore.

4. The composition of claim 3, wherein the deactivating group is a nitro group.

5. The composition of claim 3, wherein the deactivating group is a halide group.

6. The composition of claim 3, wherein the deactivating group is a cyano group.

7. The composition of claim 3, wherein the deactivating group is a carboxy group.

8. The composition of claim 3, wherein the deactivating group is a sulfonic group.

9. The composition of claim 1, wherein the dye has at least one weakly activating group positioned ortho or para to the chromophore.

10. The composition of claim 9, wherein the activating group is alkyl.

11. The composition of claim 9, wherein the activating group is aryl.

12. The composition of claim 2, wherein the dye has at least one deactivating group positioned ortho or para to the chromophore.

13. The composition of claim 12, wherein the deactivating group is a nitro group.

14. The composition of claim 12, wherein the deactivating group is a halide group.

15. The composition of claim 12, wherein the deactivating group is a cyano group.

16. The composition of claim 12, wherein the deactivating group is a carboxy group.

17. The composition of claim 12, wherein the deactivating group is a sulfonic group.

18. The composition of claim 2, wherein the dye has at least one deactivating group positioned ortho or para to the auxochrome.

19. The composition of claim 18, wherein the deactivating group is a nitro group.

20. The composition of claim 18, wherein the deactivating group is a halide group.

21. The composition of claim 18, wherein the deactivating group is a cyano group.

22. The composition of claim 18, wherein the deactivating group is a carboxy group.

23. The composition of claim 18, wherein the deactivating group is a sulfonic group.

24. The composition of claim 2, wherein the dye has at least one weakly activating group positioned ortho or para to the chromophore.

25. The composition of claim 24, wherein the weakly activating group is alkyl.

26. The composition of claim 24, wherein the weakly activating group is aryl.

27. The composition of claim 2, wherein the dye has at least one weakly activating group positioned ortho or para to the auxochrome.

28. The composition of claim 27, wherein the weakly activating group is alkyl.

29. The composition of claim 27, wherein the weakly activating group is aryl.

30. The composition of claim 1, wherein the dye is an acid azo dye.

31. The composition of claim 1, wherein the dye is a triarylmethane dye.

32. The composition of claim 1, wherein the dye is a thiazine dye.

33. The composition of claim 1, wherein the dye is a nitro dye.

34. The composition of claim 1, wherein the dye is present in the range of from 0.001 to 20%.

35. The composition of claim 34, wherein the dye is present in the range of from 0.01 to 10%.

36. The composition of claim 1, wherein the category-2 bleach comprises ammonium persulfate.

37. The composition of claim 36, wherein the category-2 bleach further comprises potassium persulfate.

38. A method for simultaneously lightening and coloring hair in a single step, comprising the steps of: providing a composition comprising a category-2 bleach powder and a compatible dye selected from the group consisting of acid dyes belonging to the azo, triarylmethane, thiazine and nitro chemical classes and basic dyes belonging to the triarylmethane, thiazine and nitro chemical classes; mixing the composition in a hydrogen peroxide solution to yield a smooth cream; and applying the smooth cream to the hair to be lightened and colored.

* * * * *